United States Patent [19]

Broussard et al.

[11] 4,154,084

[45] May 15, 1979

[54] COAL-SHALE INTERFACE DETECTION

[75] Inventors: Peter H. Broussard, Huntsville; John L. Burch, Decatur; Edward J. Drost, Huntsville; Richard J. Stein, Huntsville, all of Ala.

[73] Assignee: The United States of America as Represented by the Administrator, National Aeronautics and Space Administration, Washington, D.C.

[21] Appl. No.: 848,420

[22] Filed: Nov. 3, 1977

[51] Int. Cl.² ............................................. G01N 3/48
[52] U.S. Cl. .......................................... 73/12; 73/82
[58] Field of Search ................... 73/12, 78, 79, 81, 82, 73/84; 299/1

[56] References Cited

U.S. PATENT DOCUMENTS

| | | | |
|---|---|---|---|
| 3,759,085 | 9/1973 | Wilson et al. | 73/82 X |
| 3,782,365 | 1/1974 | Pinna | 73/81 X |

OTHER PUBLICATIONS

Konovalov et al., Stands for Impact Testing, Ind. Lab. (USA), vol. 38, No. 10 (Oct. 1972), pp. 1273-1274.

Primary Examiner—Charles A. Ruehl
Attorney, Agent, or Firm—George J. Porter; John R. Manning; L. D. Wofford, Jr.

[57] ABSTRACT

A penetrometer for coal-shale interface detection for use with coal cutting equipment consisting of a reciprocating hammer having an accelerometer mounted thereon to measure the impact of the hammer as it penetrates the ceiling or floor surface of a mine. Additionally, a pair of reflectometers simultaneously view the same surface, and the outputs from the accelerometer and reflectometers are detected and jointly registered to determine when an interface between coal and shale is being cut through.

2 Claims, 4 Drawing Figures

COAL-SHALE INTERFACE DETECTION

ORIGIN OF THE INVENTION

The invention described herein was made by employees of the United States Government, and may be manufactured and used by or for the Government of the United States for governmental purposes without the payment of any royalties thereon or therefor.

BACKGROUND OF THE INVENTION

1. Field of the Invention

This invention relates to the art of detection of the interface between coal and shale, and particularly to a mechanized system of detection.

2. General Description of the Prior Art

As found, coal generally lies in seams of varying height with top and bottom interfaces with shale on top and clay on the bottom. In mining the coal, it is thus important to be able to operate coal cutting machines so that cuts are made which just extend to, but not into, the shale; otherwise, all of the coal that could be mined will not be mined (if the cut falls short of the interface), or shale will be mined along with the coal (if the cut goes beyond the interface), and the quality of the coal will be adversely affected. For these reasons, it is highly desirably that coal-shale interfaces be determined with considerable accuracy. Up until now, the identification of floor-ceiling material has been by the natural senses i.e.g, seeing, hearing and/or feeling, of a miner standing close to the cutting machine. Not only is this dangerous, but because of the severe environment, the sensitivity of one's natural senses of observation are not particularly keen or reliable.

Accordingly, it is the object of this invention to eliminate the necessity of personal observation of ceiling and floor material of a coal shaft in the vicinity of a coal cutting machine and to accomplish identification of the material by an electromechanical system which can perform the identification with improved accuracy.

SUMMARY OF THE INVENTION

In accordance with this invention, a penetrometer is constructed in which a ram is reciprocally driven. One end of the ram is hardened for striking, without deformations, rock or shale. An accelerometer is attached to an opposite end region of the ram, and it provides an electrical output in the form of a pulse which has distinctive characteristics enabling a "coal" signal to be distinguished from a "shale" signal.

DETAILED DESCRIPTION OF THE DRAWINGS

Figure 1:
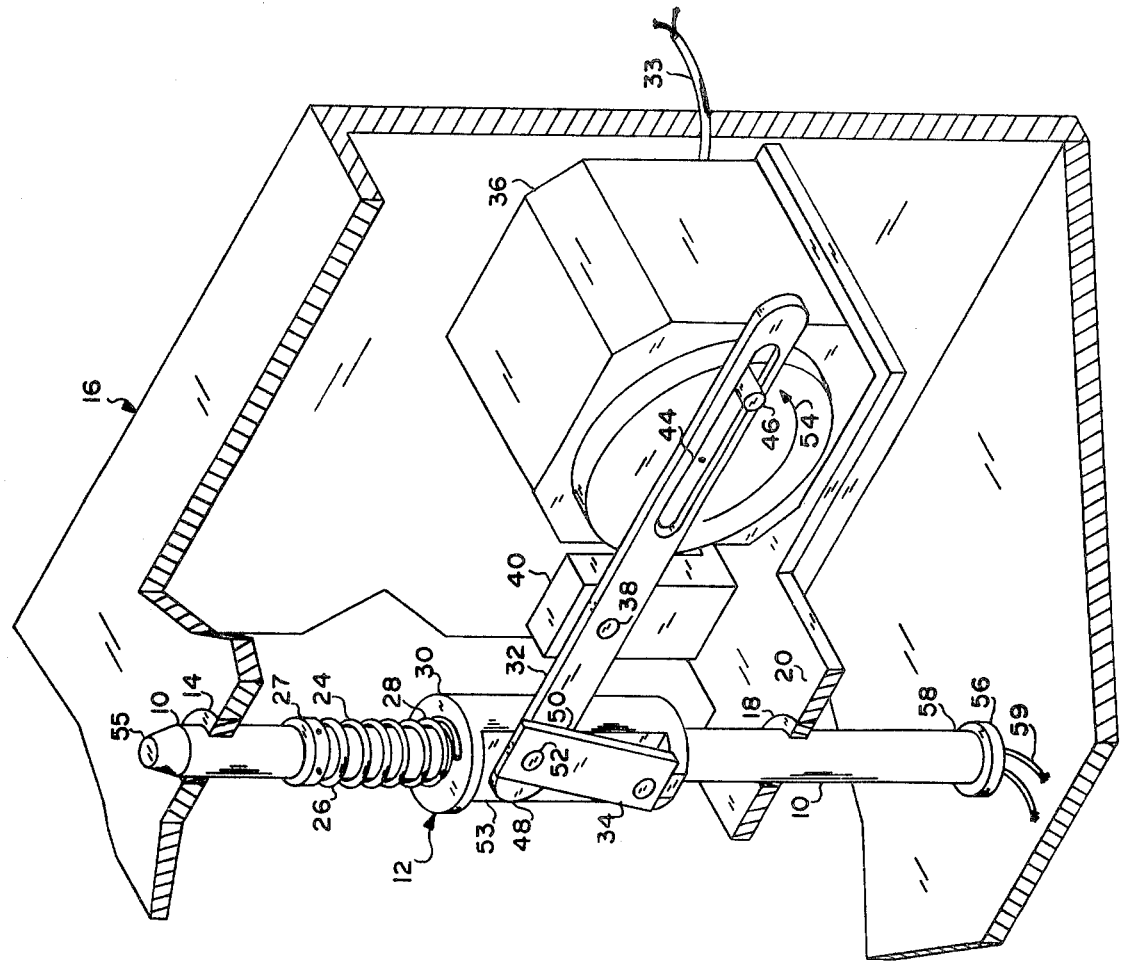
FIG. 1 is a pictorial view of a penetrometer as contemplated by this invention.
Figure 3:
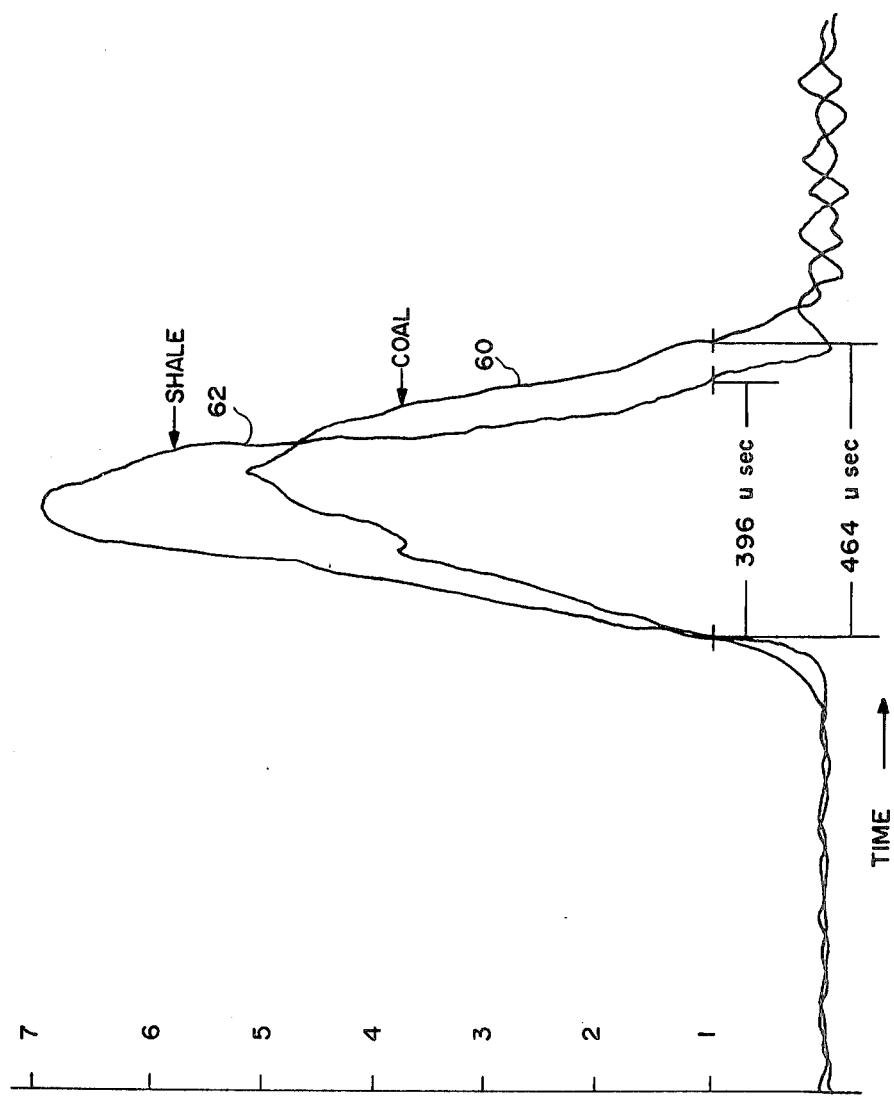
FIG. 3 is a graph illustrating the electrical response of the penetrometer shown in FIG. 1.

Referring to FIG. 1, a ram or shaft 10 of penetrometer 12 is slidably supported for reciprocal movement by bearing surface 14 of enclosure 16 and bearing surface 18 of support plate 20, in turn supported by enclosure 16. Ram 10 is reciprocally driven through spring 24, around ram 10, an end 26 of spring 24 being attached to supporting collar 27, in turn attached to ram 10. The opposite end, end 28 of spring 24, is attached to collar 30, slidably positioned around ram 10. Collar 30 is reciprocally driven through linked pivoted arms 32 and 34 of motor drive 36. Motor drive 36 has a conventional motor drive through electrical leads 33 by a power source, which is not shown. Arm 32 is intermediately pivoted by pin 38 on fixed support 40, and one end of arm 32 is driven by motor drive 36 via longitudinal slot 44 in arm 32 and concentrically mounted pin 46 of motor drive 36. End 48 of arm 32 and end 50 of arm 34 are pivotally interconnected by pin 52. Collar 30 has a flat cutout region 53 to accommodate the oscillation of arm 32 on collar 30. Thus, as pin 46 of motor drive 36 is rotated, as shown by arrow 54, collar 30 is moved along ram 10 and imparts, through spring 24, reciprocal movement of ram 10. As end 55 of ram 10 strikes a surface, spring 24 compresses. Thus, there is avoided a positive, and perhaps destructive, force between motor drive 36 and ram 10. The impact on and penetration into the floor or ceiling material of a coal mine of ram 10 is sensed by accelerometer 56 mounted on end region 58 of ram 10. Its electrical output is provided by leads 59 to the electrical circuitry illustrated in FIG. 4. FIG. 3 illustrates the response for the penetration of coal and shale. Thus, it will be noted that coal waveform 60 is of lower amplitude but has a wider base than shale waveform 62. These characteristics are employed, as will be further explained, to distinguish between coal and shale.

Figure 2:
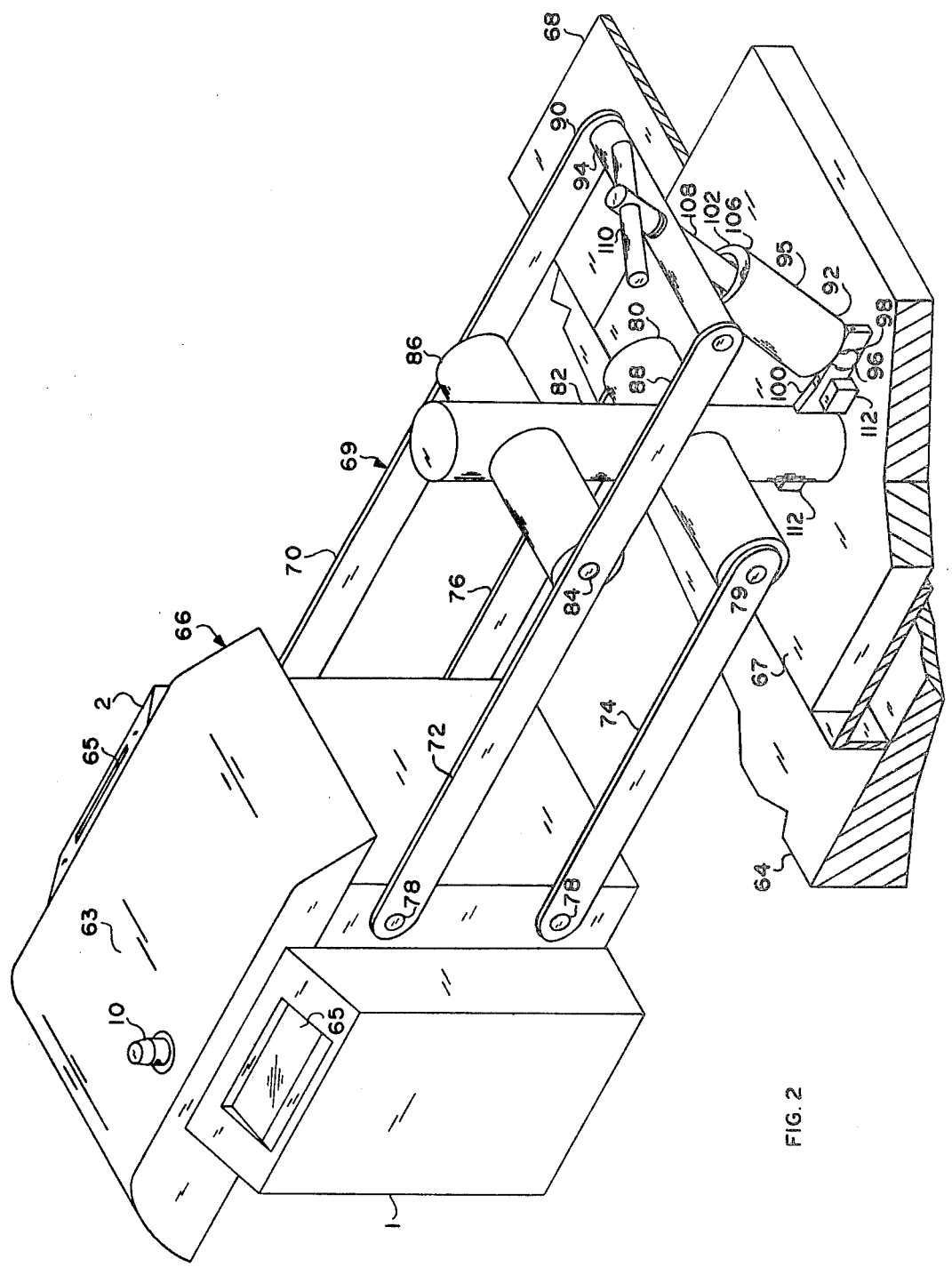
FIG. 2 is a pictorial view illustrating the arrangement of a penetrometer and two reflectometers and a system for mounting these devices.

FIG. 2 illustrates housing 63 which encloses penetrometer 12 and the mounting assembly by which housing 63 is supported by and operated as an accessory of a coal cutting machine 64, such as, for example, a longwall shearer. Also, it illustrates a second feature of this invention, which is the incorporation of two reflectometers, designated reflectometers 1 and 2. The reflectometers are conventional, being basically light responsive switches which effect an electrical switching function when a discrete level of light is reflected off of the surface of the mine being examined. Each includes a light emitting diode which provides light upward through windows 65 and a photodetector which senses the reflected light being passed back through windows 65. As shown, reflectometer 1 is positioned on one side of housing 63, and reflectometer 2 is positioned on an opposite side of housing 63, thus there being one on each side of ram 10 of penetrometer 12. To facilitate movement across the surface of a mine, the top or roof portion of housing 63 is tapered. The top or viewing surfaces of the reflectometers are sloped to eliminate debris from obscuring windows 65.

Penetrometer-reflectometer unit 66, as a whole, is mounted by virtue of base member 67 (by means not shown) on frame member 68 of coal cutting machine 64 (not shown in detail) by mounting assembly 69 which enables vertical movement of the unit without change of orientation. Mounting assembly 69 is in the form of a parallelogram employing upper parallel arm bars 70 and 72 and lower parallel bars 74 and 76. The bars are rectangularly spaced, and each is connected at one end by a pin 78 to housing 63. The opposite end of lower bars 74 and 76 are supported by pivot pins 79 through cross bar 80 on column 82, attached to base member 67. Upper bars 70 and 72 are longer than lower bars and are intermediately attached by pivot pins 84 to cross member 86 on column 82. As shown, the distance of all bars between housing 63 and cross bars are identical.

An additional function of mounting assembly 69 is to spring bias penetrometer-reflectometer unit 66 against a surface of a mine (e.g., a roof), and this is effected by a lever formed of extensions 88 and 90 of upper parallel bars 70 and 72 and spring bias assembly 92. The ends of extensions 88 and 90 are connected by cross arm 94, and spring bias assembly 92 is coupled between cross arm 94 and base member 67. Spring bias assembly 92 employs a tubular spring enclosure 95 which has a lower hook 96 connected through opening 98 to gusset 100 on base member 67. A spring 102 is coiled within tubular spring enclosure 95 and attached to tubular spring enclosure 95 at an upper end 106. The lower end of spring 102 is axially engaged by adjustment shaft 108, which shaft is threaded into cross arm 94, as shown. Then, by rotation of handle 110 of shaft 108, the levered position of mounting assembly 69 may be varied and typically would be adjusted to effect a light but constant engagement between penetrometer-reflectometer unit 66 and the surface of a mine. In order to provide a limited, rotation of column 182, and thereby a following movement by penetrometer-reflectometer unit 66, column 82 is rotatable on base member 68, but is limited by column mounted stops 112 and gusset 100.

Figure 4:
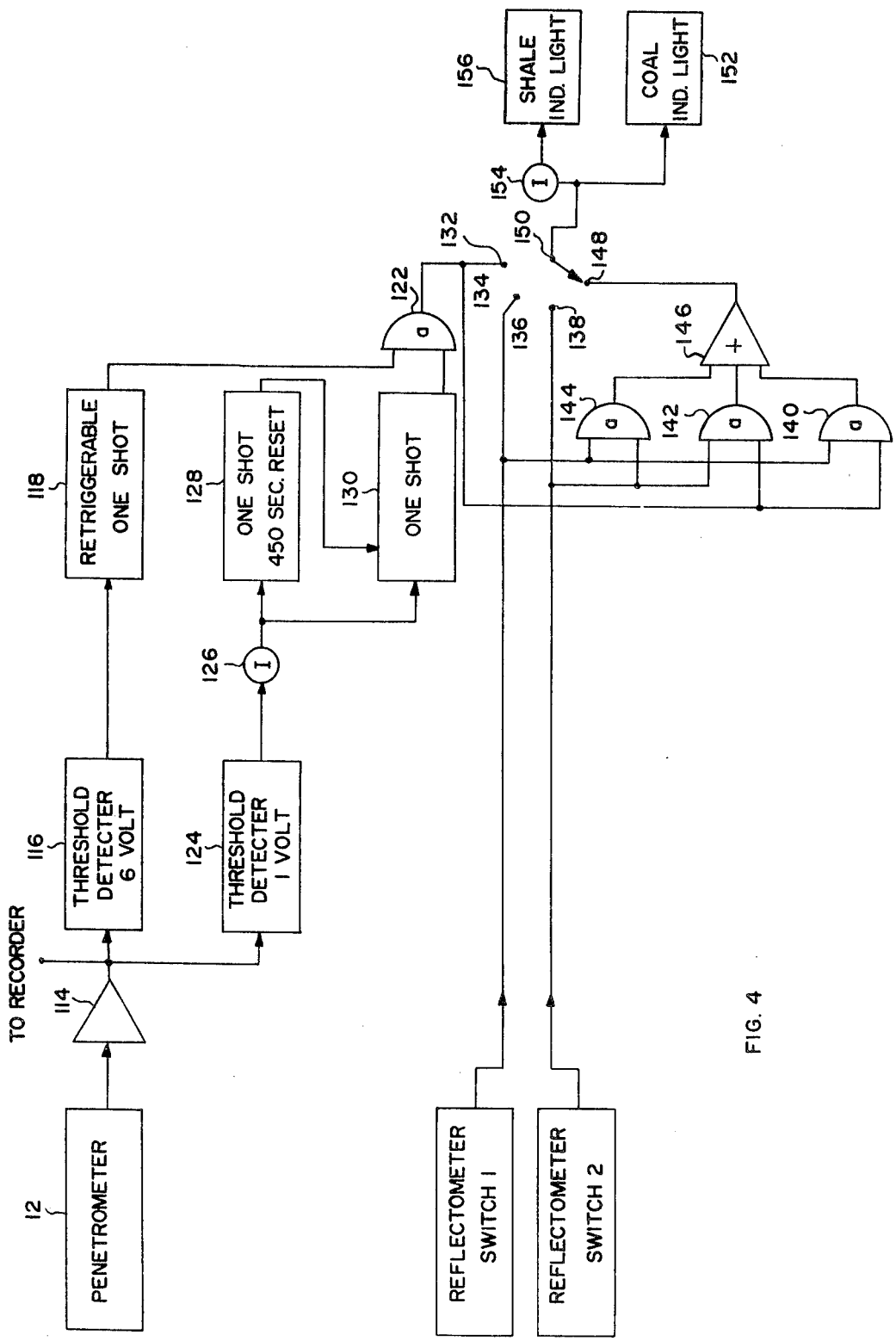
FIG. 4 is an electrical block diagram of the system of this invention.

Referring to FIG. 4, the electrical output of penetrometer 12, obtained from accelerometer 56, is amplified by amplifier 114, and in one instance the amplified signal provided to threshold detector 116. A typical response of the output of amplifier 114 is illustrated in FIG. 3 wherein waveform 60 is illustrative of a signal from the impact of ram 10 on coal, and waveform 62 is illustrative of a signal from the impact of ram 10 on shale. Threshold detector 116 is simply an operational amplifier wherein the signal input is applied to one input terminal, and an adjustable bias is applied to the other input terminal; and thus by adjustment of bias, the amplifier will provide one output state until the input signal reaches a selected level and then provide another state. In this case, the selected level is chosen, for purposes of illustration only, at 6 volts, and this will correspond to a signal level as shown in FIG. 3 just above the anticipated maximum signal from penetrometer 12 when impacted against coal.

The output of threshold detector 116 is fed to retriggerable one-shot 118 which is retriggered at the rate of impact penetrometer 12. One-shot 118 is triggered on by an output of threshold detector 116, indicating the presence of a signal responsive to the impacting of penetrometer 12 on shale. So long as a shale indicating signal is applied to one-shot 118 before it normally rests, there will remain, constantly, as an output of one-shot 118, a "low" or 0 state which is applied as one input to two-input AND gate 122. Thus, with this posture, AND gate 122 is not enabled by this signal. However, when the input signal at threshold detector 116 is below 6 volts, the retriggerable one-shot will not be retriggered on; and its output will be at a "high" or true state, which will enable AND gate 122 to pass a "coal" signal if coal is otherwise identified by the circuitry.

To further identify coal, a second output of amplifier 114 is applied to threshold detector 124, a 1-volt threshold detector, it being adapted to provide a "high" or true output state when the input signal exceeds the 1-volt level. The 1-volt level of the threshold signal is chosen as a level which is above normal noise conditions. For purposes of circuit compatibility with the circuitry to follow, the output of threshold detector 124 is inverted by inverter 126, and the signals that follow have na opposite polarity to those shown in FIG. 3.

Significantly, at the 1-volt level (with the present circuitry), and as shown in FIG. 3, the signal width or duration is greater for coal (waveform 60) then for shale (waveform 62). Thus, the duration of a coal derived signal is indicated as 464 microseconds, and a coal derived signal is indicated as 367 microseconds. Accordingly, a dividing line for comparison has been set at 450 microseconds, and one-shot 128 includes time constant circuitry to cause it to remain in an "on" state for 450 microseconds after it has been triggered, it being triggered by a negative going, leading, edge of the pulse signal output of inverter 126. The output of one-shot 128 is applied as a 450-microsecond disabling input to one-shot 130. Additionally, the pulse output signal of inverter 126 is applied to one-shot 130 which is triggered by the positive, trailing, edge of the pulse signal in the absence of the disabling 450-microsecond signal. Accordingly, if the trailing edge of the pulse signal arrives more than 450 microseconds after the leading edge, which would be the case for a coal signal, one-shot 130 is triggered to provide a "true" input to AND gate 122. Then, assuming that threshold detector 116 acknowledged that the amplitude of a signal is not greater than 6 volts, and thus retriggerable one-shot 118 is not triggered, both inputs to AND gate 122 will be "true"; and a "true" or "coal" indicating signal will be supplied as a "coal" signal to terminal 32 of selector switch 134.

In the event that either threshold detector 116 had indicated a level in excess of 6 volts, or the duration of the signal had been less than 450 microseconds, the output of AND gate 122 would not have become "true", and there would have been indicated on terminal 120 a 0 or "shale" signal.

Reflectometers 1 and 2 also provide an indication of the presence of coal or shale, and operate by virtue of the observation that the reflected light from shale is about three times greater than that from coal. The reflectometers are identical, and as stated above, each comprises a light responsive switch. In order to provide a "high" or "true" output responsive to the presence of coal in keeping with the output of the penetrometer portion of the circuitry, switching means are included in each penetrometer to connect to its output a "high" or "true" output for conditions of low light states. With a high light state, the reflectometers are adapted (as by opening a bias circuit) to provide a 0 output, indicative of shale.

The output of reflectometer 1 is connected to terminal 136 of selector switch 134, and the output of reflectometer 2 is connected to terminal 138 of this switch. Thus, there would be present on switch terminals 132, 136, and 138 separate coal-shale indicating signals derived, respectively, from penetrometer 12, reflectometer 1, and reflectometer 2. To further improve the accuracy capability of the system, these three signals are supplied to a voting circuit which provides as an output a signal representative of the majority signal state. Accordingly, each signal is applied to an input of each of two of three AND gates of the circuit. Thus, the penetrometer signal from terminal 132 is connected to an input of AND gates 140 and 142, the reflectometer 1 signal from terminal 136 is connected as an input to AND gates 140 and 144, and the reflectometer 2 signal from terminal 138 is connected as an input to AND gates 144 and 142. The outputs of the AND gates are connected as inputs to OR gate 146, and its output is connected to terminal 148 of selector switch 134, at which terminal a signal representative of the majority signal would appear.

To further examine the voting circuit, and with the selector switch operated as shown to provide a voted output on terminal 148, it is to be noted that each of the three significant coal-shale signals appear at terminals 132, 136, and 138 and are "high" or true when coal is detected, and "low" or 0 when shale is detected. Thus, with an output from each terminal being connected to an input to two of the three AND gates 140, 142 and 144, it is clear that when there occurs a "high" or "coal" indicated output on at least two of the terminals, at least one of these AND gates will be made "true" and provide an output to OR gate 146. When this occurs, OR gate 146 will provide a "true" output through terminals 148 and 150 of selector switch 134 to coal indicator light 152 to cause it to be illuminated. On the other hand, in the event that only one of the detection signals is "true", or none of them are "true", then all of the outputs of AND gates 140, 142 and 144 will be false, and there will be a "0" output of OR gate 146, which when inverted by inverter 154, will provide a "true" or high input to shale indicator light 156, causing it to be turned on. Of course, with a 0 output applied to coal indicator light 152, it would not be illuminated. While AND and OR gates are employed in the illustrated circuitry as logic elements, the more common NAND gate may be employed in their stead.

If selector switch 134 is operated to provide, as it may be, an output from a single detection device, only that signal will be effective in providing a coal or shale signal from selector switch 134, and the indication circuit will be operated as described, but responsive only to a single detection signal.

From the foregoing, it will be appreciated that this invention provides a practical electro-mechanical system for accurately distinguishing between shale and coal surfaces in a mine without the need of a human observer. Further, it provides for separate and combined utilization of two forms of detection apparatus to enable improved accuracy over widely varying conditions.

Having thus described our invention, what is claimed is:

1. A penetrometer for coal-shale interface detection comprising:
    an elongated ram;
    a frame and bearing means supported by said frame for engaging and slidably constraining said ram for movement parallel to the longitudinal dimension of said ram;
    a hard surfaced end on one end of said ram;
    drive means for repeatedly reciprocally moving said ram along a line parallel to the longitudinal dimension of said ram wherein said drive means includes linear force means and spring means coupled between said linear force means and said ram for applying movement to said ram, and wherein said linear force means comprises:
    a. a motor and an eccentric member driven by said motor;
    b. a lever arm and pivot for intermediately pivoting said lever arm;
    c. one end region of said lever arm being slidably coupled to said eccentric, whereby said lever arm is oscillated about said pivot;
    d. coupling means for coupling an opposite end region of said lever arm to said spring; and
    accelerometer means coupled to said ram for providing an electrical output representative of the rate of change of velocity of said ram responsive to said hard surfaced end of said ram striking a material, and thereby provide a signal indicative of the presence of coal, and, alternatively, shale.

2. A penetrometer as set forth in claim 1 wherein said coupling means comprises:
    a collar positioned around and slidably mounted on said ram;
    pivot means for connecting said opposite end of said lever arm to said collar; and
    said spring being connected between said collar and said ram.

* * * * *